United States Patent [19]

Oechsle, III

[11] Patent Number: 4,570,270
[45] Date of Patent: Feb. 18, 1986

[54] POLYURETHANE COMPOSITIONS AND THEIR USE AS LUTING AGENTS

[76] Inventor: Sixtus J. Oechsle, III, 3907 Henry Ave., Philadelphia, Pa. 19129

[21] Appl. No.: 637,714

[22] Filed: Aug. 3, 1984

Related U.S. Application Data

[62] Division of Ser. No. 419,999, Sep. 20, 1982, Pat. No. 4,477,604.

[51] Int. Cl.$^4$ .................................................. A61F 1/24
[52] U.S. Cl. ...................................... 623/18; 623/22; 623/23; 128/92 C; 128/92 CA
[58] Field of Search .................... 3/1.912, 1.913, 1.91; 128/92 R, 92 CA, 92 C; 523/116, 112

[56] References Cited

U.S. PATENT DOCUMENTS

| | | | |
|---|---|---|---|
| 3,255,747 | 6/1966 | Cochran et al. | 128/92 R |
| 4,065,817 | 1/1978 | Branemark et al. | 3/1.91 |
| 4,267,299 | 5/1981 | Oechsle | 528/65 |
| 4,357,716 | 11/1982 | Brown | 128/92 CA |
| 4,477,604 | 10/1984 | Oechsle | 523/116 |
| 4,491,987 | 1/1985 | Park | 3/1.91 |

Primary Examiner—Helen M. McCarthy
Attorney, Agent, or Firm—Robert S. Bramson

[57] ABSTRACT

Polyurethane and poly(urea)urethane compositions as specified below are utilized as luting agents, for filling cavities or spaces in human or other animal bones, and are introduced in liquid form and formed in situ to create a polyurethane or poly(urea)urethane elastomer which is relatively compatible with the surrounding tissue, has good adhesive properties, low friability, and good tear and tensile strength. The invention includes the polyurethane and poly(urea)urethane compositions disclosed and their uses in the performance of surgery in human beings and other animals. The polyurethane and poly-(urea)urethane compositions are produced by the reaction of an "A" component prepolymer which is the reaction product of a diiosocyanate with a diol or polyol, and a two element "B" component, which may be any of the polyols used in producing the "A" component prepolymer or a relatively short chain diol or triol or a diamine (in the case of a poly(urea)urethane) or combinations thereof. One element of the "B" component is relatively highly reactive and reacts with a majority of the "A" component. The other element of the "B" component is less reactive and acts as a bulking agent to facilitate mixing of the two components.

3 Claims, No Drawings

POLYURETHANE COMPOSITIONS AND THEIR USE AS LUTING AGENTS

This application is a division of application Ser. No. 419,999, filed 09/20/82 now U.S. Pat. No. 4,477,604.

BACKGROUND OF THE INVENTION

1. Field of the Invention

The invention relates to the field of surgery for human beings and other animals in which elastomeric materials are utilized as adhesives and as fillers to occupy spaces produced or permitted during surgery, particulary where bone replacement prosthenses are being inserted in a human being or other animal.

2. Description of the Prior Art

Artificial bones, particularly joints, have been used for many years as replacement parts for human beings and other animals. For example, a patient with degenerative arthritis at an advanced state may not be able to use a degenerated joint, so that it is often necessary to replace a degenerated joint with an artificial joint. Some of the common joints which are surgicially replaced for these purposes are knees, shoulders, hips, fingers, toes and elbows. Each type of joint requires a different type of joint replacement member. However, all types of joint prostheses share some common characteristics. The material of the prosthesis is usually metal, although ceramics or other materials may be used. For example, titanium and various types of chromium steel alloys are commonly used for prostheses. The prostheses may be solid, or they may be fenestrated (formed with windows) to allow the regenerative bone tissue to form through the windows in the prosthesis, to provide added stability and strength to the bond between the bone and the prosthesis, and to allow the luting agent to extend through the window to provide a more secure affixation in place of the prosthesis.

A prothesis, as inserted for use, includes a narrow, elongated shank which projects into a generally similarly shaped, excavated cavity which the surgeon creates in the bone into which it is to be anchored. The area which is excavated to provide the space for the prosthesis shank is called the medullary cavity. The size of the medullary cavity is not necessarily proportionate to the size of the shank and it may be substantially larger. The reason for this is that the shanks come in limited numbers of sizes, and when the surgery is performed, all of the soft cancellous tissue in the bone proximate the shank must be excavated in the area of the shank, in order to provide the most secure bond between the bone and the prosthesis.

The luting agent acts as a filler, to fill the space between the cortical or reamed section of the bone and the shank of the prosthesis. This function is obviously critical for several reasons. First of all, the material used as a luting agent must be relatively liquid or amorphous in its initial state, so that it can easily be inserted in and fill completely the medullary cavity which has been formed. It must also, when cured, conform closely and snugly to the shape of the shank of the prothesis. The luting agent must also provide good adhesive properties to the prosthesis and to the human or other animal bone in question. The luting agent, during the polymerization reaction in which it solidifies and hardens, must not produce an excessively high exotherm, because the exotherm could do enormous heat damage to the adjacent tissue. The luting agent should desirably have isotropic elastic properties which are similar to the elastic properties of the contiguous bone, so that shock absorption and therefore stress in the area, when the prothesis is in use (as, for example, when a person with a knee prosthesis is running) is substantially uniformly distributed through the bone and through the hardened luting agent, a condition which is necessary to maintain maximum bone strength. Lastly, the luting agent should not be friable, because particles which break away from a luting agent are foreign bodies within the joint, and can cause severe abrasive tissue damage.

Many polymeric materials have been attempted for use as luting agents, some with reasonable success. However, none of the luting agents of the prior art is capable of achieving satisfactorily all of the foregoing desiderata. Each has numerous shortcomings.

Polymethylmethacrylate is the most commonly used luting agent. Its limitations are: it is exothermic in use, producing temperatures of approximately 100° C. which can cause tissue trauma; it is brittle and, under the stress of use, can fragmentize and these fragments can accelerate the wear of the adjacent components of the prosthesis and cause tissue damage; it shrinks substantially during polymerization, reducing the intimate contact surface area between the luting agent and the bone and creating stresses within the polymer itself which increase the likelihood that the polymer will disintegrate, break down and fragmentize; and it may cause systemic hypotension during insertion.

In joint replacement surgery, there is a failure rate of almost one hundred percent of all joint replacements within five years after they have been inserted. This failure rate is caused by the loosening of the prosthesis as a result of the loosening of the luting agent, due to shrinkage, loss of physical properties and physical disintegration. Also, polymethylmethacrylate is not an elastomeric material, so that with the normal stresses to which joints are subject during extensive use, the polymethylmethacrylate cannot adapt, causing it to fracture and break apart.

There are a couple of other materials which have been utilized as luting agents to a limited extent and without particular success. One of these is a material called "Ostamer," which is essentially a rigid polyurethane foam, formed by the reaction of toluenediisocyanate and water, and which has been used to repair bone fractures. In its use, several substantial parallel grooves are sawed into the broken bone in the direction of the elongated axis of the bone and extending beyond the broken areas of the bone. Metal rods are inserted in these grooves and held in place by metal bands proximate the ends of these rods. The Ostamer is then inserted to fill the sawed apertures in the bone and to hold the metal rods in place, forming a rigid polyurethane foam to hold the fractured ends together. This use of Ostamer was not acceptable for several reasons, including the very high exotherm produced during formation of the rigid polyurethane foam, which caused extensive tissue damage. Also, the raw materials used in creating the Ostamer are toxic and the polymer, when formed, is not biostable. Therefore, this procedure is no longer in use.

Polyester has also been attempted for use as a luting agent, without satisfactory success, because of its high exotherm, its high shrinkage, its extreme brittleness, and its chemical instability at body temperatures.

Reference is made to U.S. Pat. No. 4,267,299, which discloses 100% solid polyurethanes and poly(urea)urethanes formed by spray application.

SUMMARY OF THE INVENTION

The invention comprises the use of certain polyurethane-forming and poly(urea)urethane-forming materials, to produce, by chemical reaction in situ and with a relatively low exotherm, a "100% solid" elastomer with isoelastic behavior whereby stresses in the elastomer are substantially uniformaly distributed throughout the elastomer; compatibility, whereby the elastic properties of the elastomer can be varied to closely match the elastic properties of the adjacent bone; low friability, whereby the elastomer after long periods in place will not substantially disintegrate and cause inflammation, tissue reaction or abrasion of the adjacent prosthesis when the prosthesis is a polymeric material such as polyethylene; lack of shrinkage in its formation; and ability to be poured readily into the medullary cavity and react rapidly (a brief "gel time") to retain physical integrity to support the prosthesis shank firmly in position within seconds after the elastomer's components are mixed, to prevent displacement of the shank from position. These desirable features are obtained by the use of certain components which form 100% solid polyurethane and poly(urea)urethane elastomers, which may also be formed as copolymers with other elastomeric materials, such as polydimethylsiloxane and acrylics.

As used herein, a "100% solid" polyurethane or poly(urea)urethane is one which, after its formation is complete, is substantially completely solid (as contrasted to a liquid or a viscous, flowable material).

The polyurethane or poly(urea)urethane must be formed from certain specific types of reactants, in order to assure that the reaction product is formed with a tissue-tolerable exotherm and with the desirable physical properties. The "A" component prepolymer which is used to form the elastomer is the reaction product of one or more diisocyanates with one or more diols or polyols.

The "B" component may include any of the polyols utilized in preparing the "A" component prepolymer and/or a diamine as curing agent and any suitable short chain diol or triol as reactive fillers to form a 100% solid polyurethane or poly(urea)urethane with the desirable chemical and physical properties of this invention.

It is desirable to use the same polyol in the curing agent of the "B" component as is used in forming the "A" component because there is less randomness in the resulting elastomer when this criterion is followed, thus resulting in more uniform physical properties throughout the elastomer.

One purpose of the selection of the particular reactants of the "A" component and the "B" component is to produce a polyurethane or a poly(urea)urethane which is formed from components which are liquid at room temperature, without the use of a solvent, since solvents are very harmful to animal tissue. The polyol is utilized as a "filler" or bulking agent to provide the requisite volume ratio between the "A" and "B" component and will participate to a limited extent in the polymerization reaction to provide good, uniform physical properties throughout the elastomer. The volume ratio of "A" to "B" component used is important in the practice of this invention, to permit easy handling and intimate mixing of the two components and a 1:1 ratio is most desirable.

The curing agent of the "B" component is the principal reactive agent with the "A" component for the formation of the elastomer, and will function as a cross-linking agent or chain extender or both for the "A" component and will substantially completely react with the NCO-groups in the "A" component within about two to five minutes after the "A" and "B" components are mixed. Thus the curing agent is said to be "highly reactive."

The "filler" is also reactive with the NCO-groups of the "A" component, but is substantially less reactive. Thus a relatively large quantity of filler may be used with a small quantity of highly reactive curing agent to provide the required volume of "B" component to mix radily with the "A" component.

It will be appreciated that a large number of combination of isocyanates, diols, polyols and other curing agents come within the parameters of this invention. Not all combinations of disclosed components will produce the desired results and will combine the desired chemical and physical properties. Such considerations as pharmacological acceptability, working time, "gel time," cure time, exotherm, isoelasticity and load bearing criteria will all be taken into account in selecting the proper combination of components for a particular application or group of applications. These considerations are all within the purview of a skilled polyurethane chemist.

As used herein, the "gel time" is the time which elapses after an "A" component and "B" component are mixed until the resulting elastomer has cured sufficiently that it has a consistency resembling warm table butter.

OBJECTS OF THE INVENTION

It is therefore an object of this invention to provide novel polyurethane and poly(urea)urethane luting agents, and processes for their use, for use in filling bones in humans and other animals which have the advantages of:

(1) Being pharmacologically acceptable;
(2) Being easily poured in liquid form at room temperature;
(3) Readily forming a "gel" to provide substantial physical support to a prosthesis shortly after its insertion and having a gel time preferably of about five to ten minutes;
(4) Reacting to create a relatively low exotherm, not to exceed approximately 150° F., to avoid or minimize damage to tissue.
(5) Permitting variable compositions of elastomer to be used to match the elastomeric properties of the elastomer with those of the adjacent bone tissue, to avoid damage to that bone tissue in use and to provide an isoelastic interface between the bone and the elastomeric luting agent;
(6) Possessing good physical properties of shear strength, elasticity and tensile strength;
(7) Not shrinking significantly with the passage of time; and
(8) Being relatively unfriable, and not disintegrating significantly with use.

Another object of this invention is to provide a process for the affixation in situ in a human being or other animal of a prosthetic device comprising the utilization of a polyurethane or poly(urea)urethane elastomer possessing the properties described above.

DETAILED DESCRIPTION OF THE INVENTION

The invention relates to certain compositions of polyurethane and poly(urea)urethane elastomers and copolymers of such elastomers with other polymers, which are useful as luting agents for human beings and other animals, and the process of use of such elastomers as luting agents.

As used herein, the term "luting agent" means a composition which is utilized to fill space within or between elements of human or other animal bone or other tissue. This may be necessary, for example, when a prosthesis is being inserted in the medullary cavity of a bone, and may be necessary as an adhesive to fasten pieces of bone which may be fractured, without the use of a prosthetic device.

The polyurethane and poly(urea)urethanes of this invention are formed by the reaction of an "A" component, which is the prepolymer, and a "B" component, which incorporates the relatively highly reactive curing agent and a "filler." The "A" and "B" components react when mixed to form in situ the elastomeric luting agents of this invention. This chemical reaction is exothermic, giving off heat, and must be regulated to prevent too much heat from being given off in the elastomerforming reaction.

In the practice of the invention it is important to select the particular "A" component prepolymer and the particular ingredients of the "B" component curing agent and filler so that the elastomer which they produce possesses the physical properties and other characteristics which are desired for the particular application of the invention. This means that, for different applications, different prepolymers curing agents and fillers may desirably be used, and the selection of those components to achieve the desired properties is within the purview of the skilled polyurethane chemist, in view of the disclosure contained herein. The 100% solid compositions of this invention are formed by the reaction of an "A" component prepolymer and the "B" component curing agent and filler, all of which are selected to be pharmaceutically acceptable, such that:

(1) Each components is liquid and both components are relatively easily and completely pourable and miscible at room temperature, so that they will readily completely fill a medullary cavity.

(2) The components, when mixed, have a relatively short gel time, in the range from about thirty seconds to about twenty minutes, and preferably about five to ten minutes, so that within a relatively short period of time after they are mixed as a liquid, they react and form a semi-solid gel, which possesses physical properties which are intermediate the properties of the initial liquid mixture and the ultimate elastomer, thereby providing significant structural support to help stabilize the prosthetic device and minimize the likelihood of its displacement while cure of the elastomer is continuing, but after it is desirable from a patient standpoint to close the surgical incision. It is important to establish a gel time which is appropriate for the particular purpose for which a specific composition of the invention is being used. The gel time may not be too short or the elastomer will be hardened before the prosthesis is inserted and properly positioned in the medullary cavity. The gel time may not be too long or it will delay the closing of the surgical incision, which is medically undesirable. The preferable gel time is in the range from about five to about ten minutes.

(3) The components, in reacting, produce a relatively low exotherm in reacting, not to exceed approximately 150° F., and preferably not to exceed approximately 120° F.

(4) The components are miscible in a ratio of part "A" to part "B" which makes mixing easy to do and does not require precision mixing in order to achieve the desired reaction product. The preferable ratio of "A" component to "B" component is 1:1.

(5) The resulting elastomer has good physical properties of tensile, tear and shear strength.

(6) The resulting elastomer is isoelastic, so that it has substantially uniform physical properties in all directions.

(7) The resulting elastomer will not disintegrate or shrink readily with time.

It is important to note that the components disclosed herein will produce elastomers which, in some instances, will have some but not all of the desired attributes and will have them in varying degrees. The combination of qualities desired will vary from application to application. For example, if a luting agent for a knee joint is desired, physical properties, isoelasticity and slow disintegration are important properties. On the other hand, if a luting agent is desired for a finger or toe joint, good adhesion to the bone is important, and physical properties are less important since the joint withstands much smaller forces.

The "A" components of this invention are the reaction products of one or more diisocyanates with one or more diols or polyols. The diisocyanate can be, but is not limited to, tolyene diisocyanate, methylene bis diphenyldiisocyanate, 5,5' dimethyl methylene bis diphenyldiisocyanate, bitolylene diisocyanate, naphthalene diisocyanate, DDI diisocyanate, dianisidine diisocyanate, toluidine diisocyanate, xylylene diisocyanate, hexamethylene diisocyanate, paraphenylene diisocyanate or mixtures of the above.

The diol or polyol can be polytetramethylene ether glycols of molecular weights from about 500 to about 3000; polyoxypropylene glycols of molecular weights from 200 to about 6000; tetraethylene-glycol polyester glycols of molecular weight from about 400 to about 3000, such as those made from a dicarboxylic acid such as adipic, azelaic, sebacio, suberic, pimelic, glutaric, succinic, maleic, phthalic, isophthalic and terephthalic acids and a glycol such as ethylene glycol, propylene glycol, diethylene glycol or dipropylene glycol or mixtures of these acids and glycols; or polylactone glycol of molecular weight from about 500 to about 3000, such as polycaprolactone; but is not limited to these acids or glycols; polybutadienes having molecular weights in the range from about 400 to about 3,000; polyoxypropylene oxyethylene glycols of molecular weight from about 300 to about 5000; polycarbonate diols or glycols having molecular weights in the range from about 500 to about 3,000; and polyisobutylene glycols having molecular weights in the range from about 1,000 to about 10,000.

In forming the "A" component, the diisocyanate is desirably reacted in a molar ratio of from about 1.5 to about 12 moles per mole of polyol, which will result in an excess isocyanate content of from about 2.5% to about 25% by weight.

The "B" component is made up of one or more relatively highly reactive curing agents which are the primary reactant with the "A" component to form the desired elastomer. Slightly less than all of the relatively highly reactive curing agent needed to completely react with the "B" component is used, in order to allow the less reactive "filler" to participate in the urethane-forming reaction and be an integral part of the ultimate elastomer molecule. This is important because a relatively small volume of relatively highly reactive curing agent is needed to react completely with the "A" component. This volume is typically about 6–25% of the "A" component volume, so that a volumetric mixing ratio of between 20 to 1 and 4 to 1 would normally be needed for a complete reaction. It is difficult to get intimate mixing of "A" and "B" components when the volume differences (and potential viscosity differences) are so great.

The ideal volume ratio for easy and intimate static mixing of "A" and "B" components is 1:1. For this reason, the "B" component is made up of one or more relatively highly reactive curing agent in low volume plus a much larger quantity of a relatively less reactive filler, in such quantities that equal volumes of "A" component and "B" component will react to form an 100% solid elastomer in which both the curing agent and filler are chemically incorporated.

Since the curing agent reacts with most of the "A" component, it is the selection of curing agent and the quantity of curing agent which determine the gel time.

The "B" component may include as the curing agent any of the polyols mentioned above in preparing the "A" component adduct (prepolymer) or other polyol or a diamine or a combination thereof. The diamine can be, but is not limited to polyoxypropylene diamine, methylene, dianiline, methylenebis dipropylaniline, diethylated toluene diamine, toluene diamine, trimethylene bis para amino benzoate, bis (amino phenyl thio) ethane, menthane diamine and cyclohexane diamine, or mixtures of the above diamines.

The short chain diols or triols which are used as less reactive "fillers" can be, but are not limited to butane diol, ethylene glycol, diethylene glycol, triethylene glycol, tetraethylene glycol, thiodiglycol phenyldiethanolamine, phenyl diisopropanol amine, cyclohexanedimethanol, beta hydroxyethyl ether of hydroquinone or resorcinol, trimethylolpropane, trimethylolethane, glycerol and mixtures of the above diols and triols. Compounds having both amine and hydroxyl function can also be used, such as but not limited to polyglycol amine "H-163," which is sold by Union Carbide.

For purposes of this invention the preferred art for the "B" component is to use as the relatively highly reactive curing agent one or more of the polyols used in the preparation of the "A" component and a diamine with a less reactive filler which is one or more short chain diols or triols. The ratio of curing agent to filler can be varied to regulate the mixing ratio of "A" to "B" component, working life, gel time and cure time as well as exotherm and load bearing capability, and will also vary with the type of diisocyanate and isocyanate content of the chosen "A" component.

It is, of course, essential that all components of the polyurethane and poly(urea)urethane elastomers be pharmaceutically acceptable and of medical grade, so that they may properly be used in the practice of this invention. In the practice of this invention a given quantity of "A" component is initially mixed with a given quantity of the "B" component to react and form the desired elastomer. In order to make intimate mixing of the "A" and "B" components easy to do, it is preferred that the "B" component is composed of the relatively highly reactive curing agent and less reactive filler in amounts such that equal parts of "A" component and "B" component can be mixed to form the desired elastomer. Other mix ratios can be utilized and various mechanical mixers can also be used to insure accurate and complete mixing of the "A" and "B" components. However, it is preferred to use a caulking gun as a mixer and applicator in which two sealed single use tubes of "A" component and "B" component are static mixed without mechanical agitation. A conventional two-component caulking gun, made of sterilizable materials, such as stainless steel, for surgical use would be suitable and would have a variety of sizes and shapes of nozzles to adapt to the different sizes, shapes and locations of places for delivery of the elastomers of this invention.

It is also possible to mix the "A" and "B" components by hand in a sterile vessel using a hand-held mixing instrument and manually inserting the mixture into the medullary cavity with a suitable instrument.

If a caulking gun or mechanical mixer is used, only a few seconds are needed to effect satisfactory mixing. If manual mixing is used about two to three minutes should be allowed for adequate mixing. In either event the gel time of the mixture should be sufficient to permit mixing and allow adequate time for the activities of the surgeon before the incision is closed.

The particular "B" components utilized in the invention most desirably comprises a diamine, a short chain diol or triol and a relatively long chain glycol. The diamine, which is present in a relatively low quantity, which depends on the reactivity of the "A" component diisocyanate, on the order of about 1% to about 50% by weight of the "B" component, is utilized to cause a rapid initial reaction with the part "A" prepolymer and thereby to allow the mixture to gel rapidly. This feature allows the components of the invention to be inserted in a bone cavity, with the shank of the prosthesis inserted promptly thereafter. The rapid gel time allows the elastomer to "set up," holding the shank firmly in place, allowing the surgeon to commence doing the incision at that time, before the elastomer is fully cured. Particularly desirable diamines are 4 cyclohexane diamine, 4,4' methylene dianiline, 4,4' methylene bis (2.6 diisopropyl aniline), 1,8 diamino menthane, ethylated toluene diamines and polyoxy propylene diamines.

The diamine and/or relatively reactive diol or polyol is the primary curing agent and is selected to provide higher physical properties by increasing the crystalline hard segment concentration in the final polymer and a to create a maximum exotherm in the urethane-forming reaction. With an exotherm that does not exceed 150° and is preferably about 120° F., the incision can be closed when the urethane-forming reaction is not completed and the exotherm will not cause unacceptable tissue damage. Particularly desirable diols or triols for the curing agent are trimethylol propane, butane diol, 1,3 butylene glycol, diethylene glycol, triethyene glycol, tetraethylene glycol, and other systems of similar equivalent weight.

A short chain glycol may be used as a "filler" or bulking agent, to make the "B" component usable in reasonable volumes that make the "A" and "B" components easy to handle, so that 1 to 1 ratios by volume of "A" to "B" components are possible. The filler also participates in the urethaneforming reaction, so that all of the "B" components form chemical components of the final elastomer, making for a stronger, more cohesive elastomer from which components will not separate or leach out. A desirable range of filler equivalent weights is from about 300 to about 2,000.

The relative portions of curing agent and filler in the "B" component are respectively 5% to 50% and 25% to 95% by weight.

The following examples disclose preferred embodiments of the invention and should not be interpreted as limiting the scope of the invention.

EXAMPLES

Preparation of "A" Component Prepolymers

Prepolymer A was prepared using tolylene diisocyanate and polytetramethylene ether glycol of molecular weight 1000 in a mole ratio of 1.7 to 1, such that a 4.2% isocyanate content remained after reacting for 3 hours at 70° C.

Prepolymer B was prepared using tolylene diisocyanate and a polyethylene butylene glycol adipate of 2000 molecular weight in a mole ratio of 2 to 1 such that a 3.2% isocyanate content remained after reacting for 3 hours at 70° C.

Prepolymer C was prepared using methylene bis diphenyldiisocyanate and apolytetramethylene ether glycol of 1000 molecular weight in a mole ratio of 6 to 1 such that an isocyanate content of 16.8% remained after reacting for 3 hours at 70° C.

Prepolymer D was prepared using methylene bis diphenyldiisocyanate and a polytetramethylene glycol of 2000 molecular weight in a mole ratio of 3 to 1 such that an isocyanate content of 6.1% remained after reacting for 3 hours at 70° C.

Prepolymer E was prepared using a combination of methylene bis diphenyldiisocyanate and bitolylene disocyanate in a 9 to 1 ratio and a polytetramethylene ether glycol of 1000 molecular weight in a mole ratio of 3.2 to 1 such that an isocyanate content of 8.0% remained after reacting for 3 hours at 70° C.

Preparation of "B" Components

Blend A of a polytetramethylene ether glycol of molecular weight 650 as a filler, and a relatively highly reactive curing agent of butane diol and methylene bis dipropylaniline was prepared in respective percentages of 50%, 30% and 20% by weight, by heating all three blended ingredients to 70° C., mixing them until homogeneous and allowing to cool.

Blend B of a 1000 molecular weight polydiethylene glycol ethylene glycol adipate as a filler, and a relatively highly reactive curing agent of butane diol and methylene bis dipropylaniline in respective percentages of 50%, 30% and 20% by weight was prepared in the same manner as Blend A.

Blend C of a 650 molecular weight polytetramethylene ether glycol as a filler and a relatively highly reactive curing agent of butane diol and methylene bis dipropylaniline in respective percentages of 75%, 20% and 5% by weight was prepared in the same manner as Blend A.

Blend D was prepared using the same components as blend C in respective percentages of 60%, 30% and 10% by weight.

In each instance, equal quantities of the "A" components and "B" components described above were manually mixed for about two minutes in the combinations shown in the following Table, under ambient conditions at a theoretical stoichiometry of 100%. The results are listed in the following Tables.

TABLE I

| Example | A Component | B Component | Mix Life | Work Life | Exotherm* | Shore Durometer |
|---|---|---|---|---|---|---|
| 1 | A | A | 1 Min | 5 Min | 140° F. | 70A |
| 2 | B | B | 2 Min | 10 Min | 140° F. | 70A |
| 3 | C | C | 1 Min | 12 Min | 150° F. | 55D |
| 4 | D | D | 4 Min | 30 Min | 105° F. | 85A |
| 5 | E | D | 5 Min | 60 Min | 102° F. | 90A |

*By way of comparison, commercially available polymethylmethacrylate, such as that sold as "Surgical Simplex P Bone Cement," has an exotherm of 220° F.

TABLE II

| | Comparison of Physical Properties | | | |
|---|---|---|---|---|
| | Tensile Strength (PSI) | Percent Elongation | Izod Impact (Ft. Lbs.) | Abrasion (Mg. Lost) |
| Polydimethylsiloxane | 1,000 | 500 | 9.0 | Poor |
| Polyethyleneterephthalate | 25,000 | 70 | 0.3 | 400 |
| Polyethylene | 6,500 | 450 | 10.0 | 30 |
| Polymethylmethacrylate | 8,000 | 5 | 0.4 | 325 |
| Example 1 | 1,800 | 400 | No Break | 12 |
| Example 2 | 4,000 | 300 | No Break | 10 |
| Example 3 | 3,200 | 275 | No Break | 1.7 |
| Example 4 | 2,800 | 325 | No Break | 3.0 |
| Example 5 | 3,000 | 300 | No Break | 2.5 |

The foregoing data demonstrate the improved wear properties available with the composition of this invention.

In the practice of the invention, when a patient is to have a prosthesis inserted, the surgeon will make an incision and ream out the end of the bone into which the shank of the prosthesis is to be inserted.

The excavation is than packed with a drying agent to remove blood and moisture. A clotting agent is then applied to minimize blood flow.

The "A" and "B" components are then intimately mixed, as in a surgically usable caulking gun type of applicator, in a convenient volume ratio such as 1:1. This is preferably done with the evacuation of air from the medullary cavity, by the use of a vacuum pump, as the elastomer-forming mixture is extruded into the medullary cavity in the bone. The mixture is of low viscosity as it leaves the caulking gun and flows easily into and almost completely fills the medullary cavity but in about five minutes it has gelled sufficiently to have the consistency of soft, warm table butter. This is sufficient to hold the prosthesis shank in place, so that the closing up procedure can begin. By the time that the surgical opening is completely closed, say twenty minutes later, the elastomer has the consistency of hard cheese and is almost completely cured.

Thus, it will be seen that improved luting agents providing improved physical properties with a relatively low and more tissue-tolerable exotherm are available by practising the teachings of this invention. It will be appreciated that a great variety of "A" components and "B" components and combinations thereof are possible within the teachings of this invention. These variations may be utilized to minimize cost, control gel time, improve ease of handling, obtain improved physical properties and combinations of the foregoing. However, these variations may be made by a person having ordinary skill in the art, within the scope of and in accordance with the teachings of this invention.

It is also noteworthy that the invention may be used with prosthesis materials other than stainless steel and ceramic, the particular "A" and "B" components being selected to provide good bonding to the prostheses, in addition to the other necessary physical and chemical properties.

Although the invention has been described in connection with prostheses, it it is also usable in connection with tissue-to-tissue bonding, as in mending broken bones.

Although the invention has been disclosed as comprising only a prepolymer, curing agent and filler, it is within the purview of this invention to incorporate additives in the reactants to modify the properties of the end-product elastomer or regulate the elastomer-forming reaction.

I claim:

1. A process for inserting a prosthesis into a medullary cavity in a human being or other animal comprising the steps of:
   (a) intimately admixing a pharmaceutically acceptable poly(urea)urethane-forming prepolymer and a curing agent and filler;
   (b) promptly pouring the reactants set forth in step (a) into the medullary cavity;
   (c) inserting a prosthesis; and
   (d) completing the insertion of prosthesis, and closing the incision made to permit the procedure, within a period in the range from about five to about ten minutes after the reactants are admixed.

2. A process as set forth in claim 1, wherein the exotherm caused by the reaction when the ingredients are mixed in step (a) is not greater than 150° F.

3. A process as set forth in claim 2, wherein air is removed from the medullary cavity as the reactants are poured therein.

* * * * *